United States Patent [19]

Osborg

[11] 4,286,108

[45] Aug. 25, 1981

[54] PROCESS FOR PREPARING HYDRAZINES

[76] Inventor: Hans Osborg, 80 Longview Rd., Port Washington, N.Y. 11050

[21] Appl. No.: 85,882

[22] Filed: Oct. 17, 1979

[51] Int. Cl.[3] ............................................ C07C 109/04
[52] U.S. Cl. ..................................... 564/464; 564/314; 546/311; 564/313; 564/457; 564/461; 423/407
[58] Field of Search ............................ 260/583 B, 569; 423/407; 564/314, 464

[56] References Cited

U.S. PATENT DOCUMENTS

| | | | |
|---|---|---|---|
| 3,164,635 | 1/1965 | Braude | 260/583 B |
| 3,683,026 | 8/1972 | Koenig | 260/583 B |
| 4,013,758 | 3/1977 | Osborg | 423/407 |

*Primary Examiner*—Paul F. Shaver
*Attorney, Agent, or Firm*—Kane, Dalsimer, Kane, Sullivan and Kurucz

[57] ABSTRACT

A process is disclosed for preparing anhydrous hydrazines by reacting a tertiary hydrazinium halide with a corresponding alkali metal or alkaline earth metal amide in the presence of a non-aqueous inert carrier.

13 Claims, No Drawings

PROCESS FOR PREPARING HYDRAZINES

BACKGROUND OF THE INVENTION

1. Field of the Invention

The invention relates to a process for preparing hydrazine and hydrocarbyl-substituted hydrazines.

2. Brief Description of the Prior Art

Hydrazine, phenyl-substituted and alkyl-substituted hydrazines, particularly unsymmetrical dimethylhydrazine, have become important commercial compounds for a wide variety of purposes, including as intermediates in the preparation of blowing agents, pharmaceuticals, fuels, agricultural products and the like.

Prior to my invention, a number of processes were known for the preparation of hydrazine and its alkyl-substituted derivatives. For example, the Raschig Process is a commercial synthesis of hydrazine from ammonia and sodium hypochlorite in two steps. Initially, chloramine is formed with sodium hydroxide by-product. Then the chloramine reacts with excess ammonia to form hydrazine. In the first stage, chloramine, is formed rapidly. However, in the second step the reaction of chloramine with ammonia is slow and requires heat for completion. The rate of formation of the desired hydrazine increases with temperature. As a side reaction, the hydrazine reacts with the starting chloramine to form ammonium chloride and nitrogen. This is of course undesirable and to avoid a high rate of hydrazine decomposition, the process must be carried out at high temperatures (circa 130° C.) and in large excesses of ammonia (20:1 to 30:1) to minimize the reaction of hydrazine product with chloramine reactant, and in the presence of an agent tending to retard decomposition.

The Olin process (Kobe et al., Advances in Petroleum Chemistry and Refining, Vol. 2, Interscience Pub. Inc., New York, N.Y., 1959, Chapter 9) is a modification of the Raschig process employing anhydrous ammonia. The anhydrous ammonia is injected under pressure into an aqueous chloramine solution and has the advantage wherein by the heat of dilution, the temperature of the reaction mixture is immediately raised to circa 130° C., i.e.; ideal reaction temperature for the reaction of the ammonia with the chloramine. However, heat must be provided from outside fuel sources to carry the reaction to completion and to separate the large volumes of ammonia in subsequent distillation steps. Further energy is required to remove sodium chloride and sodium hydroxide by-product and to recover the hydrazine. The hydrazine recovered is actually the monohydrate. To obtain the pure product (anhydrous) substantial further energy is required to drive off the chemically bound water.

The Schestakoff method is based on the degradation of urea by sodium hypochlorite to produce hydrazine. The reaction resembles the Hoffmann preparation of primary amines from amides. In the process, a cold aqueous solution of urea and sodium hydroxide is added to a cold aqueous solution of sodium hypochlorite. The heat of reaction increases the temperature to 100° C. where the reaction takes place at a fast rate. In the process, steam in large quantity must be used in the preparation of the urea solution (43% solution) to offset the huge endotherm of solution. The product, as in the Raschig process, is the monohydrate in low concentration (about 3%). Additional energy is required to concentrate, convert the hydrate and fractionate the final hydrazine product. Simultaneously, excessive quantities of alkali and alkali salts become useless by-products. (Ratio about 12:1 of by-products to $N_2H_4$ thus manufactured, by weight).

The Bergbau or Bayer process is not a commercial procedure although the energy requirements are not as great as in the above-described commercial processes. In the Bergbau or Bayer processes, ammonia is reacted with chlorine in the presence of a ketone to form an intermediate diazocyclopropane or ketazine. The intermediate is then hydrolyzed to the hydrazine hydrate and the latter converted to the desired anhydrous product. The same energy requirements are necessitated in recovering the hydrazine as for the commercial processes previously described.

Under the impact of the current energy crisis it has become of paramount importance to employ logistic reasoning, and to subject a manufacturing process to the requirements of logistics, as a matter of national necessity. Therefore, it becomes imperative to avoid, or at least minimize the use of energy in excess of thermodynamic requirements needed to complete a given reaction. In this connection, it must be borne in mind that the raw materials and auxiliary chemicals employed carry a liability into the process through the energy expended to produce such compounds before they are used for the present purpose, i.e.; NaOH, $Cl_2$, urea, $NH_3$, etc., consume energy in their manufacture. This energy liability must be entered into the overall equation in order to determine the degree of gain or loss in terms of energy required for the end product. Simultaneously, the weight ratio of by-products versus the desired end-product must be evaluated as an important factor in the overall logistics of a process. Many of the above-described problems of the prior art were solved by the Osborg process described in U.S. Pat. No. 4,013,758. However, it will be appreciated that the methods described therein require the availability of very low temperatures and capabilities to provide an energy input over a wide temperature range because of the type and number of diverse reaction steps.

Further, practically all commercialized methods lead to hydrazine hydrate, an exothermic chemical compound, because they are conducted in an aqueous medium.

By the nature of the process of the present invention, minimal energy requirements are made providing a more direct method offering advantages in economy and saving of national sources. In addition anhydrous hydrazine and hydrocarbyl-substituted hydrazines are obtained in high yields, readily separated from the reaction mixture by conventional techniques such as distillation.

SUMMARY OF THE INVENTION

The invention comprises a process for preparing anhydrous hydrazine and hydrocarbyl-substituted hydrazines, which comprises; reacting a tertiary hydrazinium halide with a compound selected from the group consisting of an alkali metal amide, an alkaline earth metal amide, a hydrocarbyl-substituted alkaline metal amide and a hydrocarbyl-substituted alkaline earth metal amide, in the presence of a non-aqueous inert carrier which may be a liquid or a solid.

The term "hydrocarbyl" as used herein means the monovalent moiety obtained upon removal of a hydrogen atom from a parent hydrocarbon. Representative of hydrocarbyl are alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomeric forms thereof; aryl of 6 to 25 carbon atoms, inclusive, such as phenyl, tolyl, xylyl, napthyl, biphenyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like.

The term "alkali metal" is used herein in its normally accepted sense as embracive of lithium, sodium, potassium, rubidium and cesium.

The term "alkaline earth metal" is used herein as embracive of magnesium, calcium, barium and strontium.

The term "non-aqueous inert carrier" as used throughout the specification and claims means a liquid solvent or a liquid or solid carrier vehicle for the reactants employed herein and which does not enter into or otherwise adversely affect the desired course of the reaction and which is substantially free of water. By "substantially free of water" I mean having less than 1% by weight water, preferably less than 0.1%. Illustrative of such carriers are dried kerosene (preferably of low sulfur content and freshly distilled), trialkylamines such as tripropylamine and tributylamine, mixtures thereof and the like.

In a preferred embodiment process of the invention, the carrier is selected to be the same compound which is a by-product (or co-product) of the reaction which comprises the process of the invention. For example, if the tertiary hydrazinium halide reactant employed in the process of the invention is a tertiary alkyl hydrazinium halide, then a by-product of the process will be a trialkylamine. In that case, the preferred carrier employed in the process of the invention will be the same trialkylamine so that the reaction product mixture will eventually contain the same trialkylamine as a carrier and a by-product. This facilitates eventual separation of the desired hydrazine product.

DETAILED DESCRIPTION OF THE INVENTION

The process of the invention is carried out by reacting a tertiary hydrazinium halide with an alkali or alkaline earth metal amide under substantially anhydrous conditions. Although the mechanism of the reaction has not been established, we propose that it may proceed according to the schematic formula:

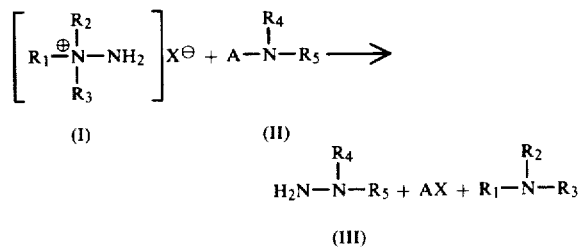

wherein the compound of formula (I) represents a tertiary hydrazinium halide, $R_1$, $R_2$ and $R_3$ are each independently hydrocarbyl, $R_4$ and $R_5$ are each selected from the group consisting of hydrogen and hydrocarbyl, A represents an alkali metal or an alkaline earth metal and X is halogen. The term "halogen" as used herein is embracive of chlorine and bromine.

The proportions of reactants of the formulae (I) and (II) employed in the process of the invention is not critical and may vary over a wide range. A slight molar excess of the amide of formula (II) present in the reaction mixture may be advantageous.

The proportion of inert carrier employed is not critical. Advantageously the proportion of carrier is from about 50 to about 1,000 percent by weight of the reactants (I and II).

The reaction, described in the above reaction scheme is carried out advantageously at atmospheric pressures although super-atmospheric pressures may be employed to speed reaction, improve yields or to facilitate the use of a carrier which would otherwise ordinarily not be a liquid at the temperature selected for carrying out the reaction.

Although the process of the invention may be carried out over a broad range of temperatures, i.e.; from about $-10°$ C. to $200°$ C., the process of the invention is preferably carried out by first admixing the hydrazinium salt (I) and the inert carrier at any convenient temperature. Then, the amide (II) is added at an elevated temperature of at least $50°$ C., and then heated rapidly, preferably within the range of from about $50°$ C. to $200°$ C., most preferably, the temperature is within the range of from about $120°$ C. to $180°$ C. In a particular preferred embodiment, the mixture of halide (I) and inert carrier are degassed and heated to $50°$–$150°$ C. prior to addition of the amide, followed by continued rapid heating to $180°$ until evolution of hydrazine has ceased. The order of addition of reactants is not critical. However, it is advantageous to mix intimately the hydrazinium halide (I) with the inert carrier material first and to add the amide (II) to the resulting mixture also, preferably integrated or ground into the carrier material. Conventional mixing equipment may be employed.

Generally, the reaction is complete within about 30 minutes or less. Progress of the reaction may be observed by employing conventional analytical instruments to determine the disappearance of reactants and the appearance of product of the formula (III). Upon completion of the reaction, the desired hydrazine of formula (III) may be separated from the reaction mixture by conventional techniques such as by distillation and like techniques. Alternatively, the product hydrazines (III) may be removed as formed in the reaction mixture by the same conventional methods of separation.

In a preferred embodiment process of the invention, the reactant amide (II) and halide (I) are introduced together in a reaction zone and then the hydrazine reaction product (III) is immediately swept clear of the reaction zone before admixture with additional starting materials occurs. This prevents undesired side reactions and raises yields considerably. It is important in such a procedure that the feed rate of the haloamine reactants (I) and (II) be controlled to provide substantially equimolar proportions so as to avoid undesirable side reactions.

Removal of the desired hydrazine product (III) from the presence of starting reactants may be accomplished most conveniently by carrying out the reaction in a continuous, pipeline type reactor of the type well-known in the art. The process is carried out by introducing the reactant (II) and reactant (I) into an inert carrier (or with an inert carrier) at the reaction zone of the reactor and carrying the resulting hydrazine product (III) away to a non-feed zone almost immediately. Advantageously the inert carrier sweeps the product hydrazine (III) from the reaction zone within less than about 30 seconds. The hydrazine product (III) may then be separated from the reaction mixture by conventional methods and techniques such as by distillation. Alternatively, the product hydrazine (III) may be simultaneously swept from the reaction zone of the reactor and distilled from the carrier, to obtain even higher product yields. The rate of bringing the reactants together may be any rate consistent with speed of the particular reaction being carried out. The zones of the pipe including the initial reaction zone may be provided with heating means to bring the reaction mixture to the desired temperature.

The pipe-line reactor may also be adapted to deposit the product (III), in inert carrier, into a cooling or distillation vessel for separation of the product as described previously.

Those skilled in the art will appreciate that the process of the invention may be carried out in batch technique or, preferably by a continuous procedure.

The reactant tertiary hydrazinium halides of formula (I) are generally well-known as is their preparation; see for example Sisler et al., Inorganic Syntheses, pages 91–95. Representative of compounds of the formula (I) are trimethylhydrazinium chloride, triethylhydrazinium chloride, triisopropylhydrazinium chloride, tri-n-heptylhydrazinium chloride, dimethylphenylhydrazinium chloride, diethylphenylhydrazinium chloride, dimethyl-p-tolylhydrazinium chloride, cyclohexyldiethylhydrazinium chloride, and the like.

The alkali metal amides and alkaline earth metal amides used as reactants in the process of the invention are also generally well-known as is their preparation. Representative of such alkali metal amides are sodamide, lithium amide, calcium amide potassium amide, sodium anilide, sodium methylamide, sodium dimethylamide and the like. Although higher yields may be obtained by use of potassium amide, sodamide is preferred in the process of the invention because of its lower cost and greater abundance. The alkaline earth metal amides are represented by calcium amide, barium amide and the like.

The following examples describe the manner and process of making and using the invention and set forth the best mode contemplated by the inventor of carrying out the invention but are not to be construed as limiting.

EXAMPLE 1

A 100 ml, 3-necked reaction flask is fitted with a mechanical stirrer, an addition funnel, a sub-surface gas inlet tube, a distillation vapor thermometer and a 20 cm glass condenser set downward for distillation.

To the condenser there is attached a receiver cooled with solid $CO_2$, to which is attached a gas outlet tube connected, in sequence, to an oil filled bubble tube, a liquid trap filled with standard sulfuric acid solution, a second bubble tube, and a final gas trap cooled to $-70°$ C.

In the flask there is placed 50 ml of kerosene (Fisher #K-10, deodorized) dried by refluxing over sodium metal), 4.0 g (0.102 mole) of sodium amide, (Fisher #S677, Lot No. 76-2097), and the mixture is heated to 150° C. in a slow stream of dry nitrogen. Heating is continued until there is no further evolution of ammonia. Dry 1,1,1-tripropylhydrazinium chloride, (19.4 g, 0.1 mole) is slurried in 20 ml of dry kerosene and placed in the dropping funnel.

The hydrazinium salt slurry is added during 8–10 minutes. A white vapor is observed in the vapor phase and the vapor temperature increased to 90° C. during the salt addition. Within 3–4 minutes evolution of white vapor ceases.

The vapor temperature increases to 100°–105° and smooth distillation at a reactor temperature of 170° C. continues for approximately 20 minutes. A total of 10–12 g of distillate is collected in the cold receiver which partially crystallizes as a white solid. The distillate is separated and found to be hydrazine in admixture with a small proportion of tripropylamine.

Titration with potassium periodate by the method of Audrieth* indicated 17.3 g hydrazine (8.1% of theory). The desired hydrazine may be separated by distillation.
*L. F. Audrieth et al. The Chemistry of Hydrazine, Wiley and Sous, New York 1951, p. 157–158.

EXAMPLE 2

Apparatus is assembled as described in Example 1. 1,1,1-tripropylhydrazinium chloride (19.4 g, 0.1 mole) and sodium-dried kerosene (70 ml) are charged to the reaction flask and heated to 50° C. in a strong stream of dry nitrogen.

Dry, powdered sodamide (4.0 g 0.102 mole) is added in a single portion. The mixture foams immediately and some liquid ammonia is collected in the receiver. The heating bath temperature is steadily increased from 50° to 176° C. during approximately 20 minutes. An initial fraction (fraction 1) is collected at a vapor temperature of 70°–80°. A second fraction (fraction 2) is collected at a vapor temperature of 105°–110° C. Both fractions partially solidify in the receiver. Upon warming, fraction 1 evolves some ammonia. The ammonia-free fraction 1 (6.74 g) partially solidified on cooling and contains 15.3% hydrazine (by periodate titration). Spot tests for hydrazine are strongly positive.

Fraction 2 (5.46 g) contains 13.1% hydrazine (by periodate titration).

The combined hydrazine yields from fractions 1 and 2 is 1.746 g (54.5% of theory). Both fractions are stable to repeated freeze-thaw cycles and the hydrazine may be further purified by cooling fractions 1 and 2 to $-70°$ and decanting tripropylamine and any co-distilling kerosene fraction.

EXAMPLE 3

Apparatus is assembled as described in Example 1, supra. To the flask there is charged 18.65 gms (0.1 mole) benzyldimethylhydrazinium chloride prepared by the reaction of chloramine with benzyldimethylamine, slurried in 20 ml. of dry kerosene. The charge is heated to 90° C. under a blanket of nitrogen gas. A mixture of sodium amide (4.0 g, 0.102 mole) in dry kerosene is heated to 150° C. in a stream of dry nitrogen and added in one portion during 5–10 minutes and heating is continued. During the addition, hydrazine is collected by distillation. Most of the product is collected at a vapor temperature of 100°–105° C. (reactor temperature 150°–170° C.).

EXAMPLE 4

The procedure of Example 2, supra., is repeated except that in place of the 1,1,1-tripropylhydrazinium chloride as used therein there is used 11.05 gms (0.1 mole) of 1,1,1-triethylhydrazinium chloride. During the addition of sodamide, a mixture of ammonia and triethylamine is collected in the trip cooled with solid carbon dioxide. After all the ammonia and triethylamine are collected, hydrazine, together with small amounts of kerosene, is collected at a vapor temperature of 100°–110° C.

EXAMPLE 5

The procedure of Example 2, supra, is repeated except that the sodium amide as used therein is replaced with 2.35 gms (0.103 mole) of lithium amide. Hydrazine is collected in the distillate at 100°–110° C.

EXAMPLE 6

The procedure of Example 2, supra., is repeated except that in place of the sodium amide as used therein, 5.67 gms (0.103 mole) of potassium amide is used and the bath temperature is maintained at 50°–125° C. Hydrazine is collected in the distillate as evidenced by titration with potassium iodate. The product is collected at 100°–110° C.

EXAMPLE 7

Dry sodium amide, (2.0 g, 0.051 mole) is mixed with dry tripropylhydrazinium chloride (9.7 g, 0.05 mole) in a porcelain boat and placed in a horizontal pyrex glass pyrolysis tube. A stream of dry nitrogen is passed over the mixture which is heated from ambient to 190° C. during the course of 30 minutes. The gas from the reaction tube is passed through a plug of pyrex wool into a series of trans cooled to 78° C. Drops of liquid which condensed in the first trap are found to contain hydrazine (by potassium iodate titration) and tripropylamine (by acid base titration for total basicity).

EXAMPLE 8

The procedure of Example 2, supra., is repeated except that the sodium amide as used therein is replaced with calcium amide, prepared by reacting calcium metal slivers in a stream of ammonia to form calcium amine (Ca[NH$_3$]$_6$) followed by heating the product slowly to 200° in a stream of nitrogen. Hydrazine is detected in the distillate by titration with potassium iodate (method of Audrieth, supra.).

EXAMPLE 9

The procedure of Example 2, supra., is repeated except that the 1,1,1-tripropylhydrazinium chloride as used therein is replaced with an equal molar proportion of 1,1,1-tripropyl-2,2-dimethylhydrazinium chloride (prepared by the reaction of dimethylchloramine with tripropylamine). The product, 1,1-dimethylhydrazine, is collected at a reaction temperature of 75°–90° C. in a stream of dry nitrogen and in a dry-ice trap. The product is identified by its boiling point (63° C.) and by potassium iodate titration.

EXAMPLE 10

Dimethylamine (4.8 g; 0.016 mole) is converted to its sodio derivative by reacting it with metallic sodium (2.3 g) in dry kerosene. Excess amine is removed by warming the mixture to 45°–50° in a stream of dry nitrogen. To the resulting sodium dimethylamine, 1,1,1-tripropylhydrazinium chloride (19.4 g; 0.1 mole) is added as a solid with vigorous stirring and the mixture is then rapidly heated to a temperature of 110°–130° C. with overhead vapors removed and condensed as a distillate.

The distillate, collected at 78° C. consists of a mixture of 1,1-dimethylhydrazine along with a small amount of tripropylamine. The desired hydrazine product may be separated by fractional distillation.

EXAMPLE 11

Purified, freshly distilled aniline (4.6 g; 0.05 mole) is converted to its sodio derivative by warming it with small portions of freshly shaved metallic sodium (2.0 g; 0.05 mole) in dry benzene (10 ml). The resulting product is added to a slurry of 1,1,1-trimethylhydrazinium chloride in refluxing benzene. Trimethylamine is evolved. After 30 minutes, the mixture is allowed to settle and the benzene layer is decanted from the solid salts. Titration of a sample of the supernatent benzene layer with potassium iodate indicates the presence of a hydrazine (phenyl hydrazine). Addition of the phenylhydrazine solution to a sample of benzald followed by recrystallization of the product yields the solid benzalphenylhydrazone (m.p. 158°) indicating the presence of phenylhydrazine in the original reaction mixture.

EXAMPLE 12

1,1-tripropyl-2-methylhydrazinium chloride is prepared from methylchloramine and tripropylamine.

Anhydrodus methylamine (CH$_3$—NH$_2$) is converted to its sodio derivative by reacting it with metallic sodium in dry kerosene. Excess amine is removed by warming the mixture to 40°–50° C. in a stream of dry nitrogen.

The 1,1,1-tripropyl-2-methylhydrazinium chloride is then added as a solid to the sodio derivative with vigorous stirring and the mixture is rapidly heated to 110°–130° C. Overhead vapors are removed and condensed as a distillate.

The distillate, collected at 80°–85°, contains 1,2-dimethylhydrazine along with a small amount of tripropylamine.

EXAMPLE 13

1,1,1-Tripropylhydrazinium chloride (19.4 g, 0.1 mole) is reacted with dry, powdered sodamide (4.0 g, 0.102 mole) in the presence of excess tripropylamine as the reaction medium. The mixture is degassed, then heated rapidly to reflux temperature (156° C.) in a stream of dry nitrogen, and the refluxing vapors are led into a glass fractionating column to yield hydrazine (bp 113°) as the distillate, tripropylamine remaining in the reaction vessel for reuse.

EXAMPLE 14

1,1,1-Tripropylhydrazinium chloride (19.4 g, 1.0 mole) and dry, powdered sodamide (4.0 g, 0.102 mole) are each slurried separately with sodium dried kerosene, and heated to 80° for at least 15 minutes in vacuum.

The degassed reactants are then combined and fed to a hot tube (or pipe) reactor containing a reaction zone heated to 180° C. Vapors from the reaction zone are led immediately to a fractionating zone, yielding hydrazine, b.p. 110°–113° C. as the overhead fraction and tri-n-propylamine as the condensate.

Hydrazine is identified in the distillate by periodate titration using the method of Audrieth, supra.

What is claimed:

1. A process for preparing anhydrous hydrazine and hydrocarbyl-substituted hydrazines, which comprises; reacting a tertiary hydrazinium halide with a compound selected from the group consisting of an alkali metal amide, an alkaline earth metal amide, a hydrocarbyl-substituted alkaline metal amide and a hydrocarbyl-substituted alkaline earth metal amide, in the presence of a non-aqueous inert carrier.

2. The process of claim 1 wherein said halide has the formula:

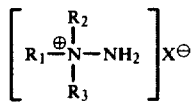

wherein $R_1$, $R_2$ and $R_3$ are each independently hydrocarbyl and X represents halogen.

3. The process of claim 1 wherein the proportion of carrier is from about 50 to about 1,000 percent by weight of the halide and the selected compound.

4. The process of claim 1 carried out at a temperature within the range of from about $-10°$ C. to $200°$ C.

5. The process of claim 1 wherein the compound selected is sodium amide.

6. The process of claim 1 wherein the halide is a chloride.

7. The process of claim 1 wherein said halide is 1,1,1-tripropylhydrazinium chloride, said compound selected is sodamide and the product is hydrazine.

8. The process of claim 1 wherein the halide is 1,1,1-trimethylhydrazinium chloride, the compound selected is sodium anilide and the product is phenylhydrazine.

9. The process of claim 1 wherein the halide is 1,1,1-tripropyl-2-methylhydrazinium chloride, the compound selected is sodium methylamine and the product is 1,2-dimethylhydrazine.

10. The process of claim 1 wherein the halide is 1,1,1-tripropylhydrazinium chloride, the compound selected is sodium dimethylamine and the product is 1,1-dimethylhydrazine.

11. The process of claim 1 wherein the halide is 1,1,1-tripropyl-2,2-dimethylhydrazinium chloride, the compound selected is sodamide and the product is 1,1-dimethylhydrazine.

12. The process of claim 1 wherein the desired hydrazine product is separated from the reaction mixture by distillation.

13. The process of claim 1 carried out at a temperature within the range of 120° C. to 180° C.

* * * * *